US00PP16658P2

(12) United States Plant Patent
Korlipara

(10) Patent No.: US PP16,658 P2
(45) Date of Patent: Jun. 13, 2006

(54) ***VERBASCUM* PLANT NAMED 'LAVENDER LASS'**

(50) Latin Name: ***Verbascum* hybrid**
Varietal Denomination: Lavender Lass

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 91 days.

(21) Appl. No.: 11/045,227

(22) Filed: Jan. 27, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—Klarquist Sparkman, LLP

(57) ABSTRACT

A new and distinct *Verbascum* plant characterized by numerous bright lavender colored flowers on numerous short, upright flowering stems, a compact habit, and excellent vigor.

1 Drawing Sheet

Botanical denomination: *Verbascum* hybrid ((*V. phoeniceum*×*dumulosum*)×*V. phoeniceum*)).

Variety designation: 'Lavender Lass'.

The present invention relates to a new and distinct cultivar of *Verbascum* hybrid, and given the cultivar name 'Lavender Lass'. *Verbascum* is in the family Scrophulariaceae.

This new cultivar originated from a cross between *Verbascum* 'Jackie', an unpatented plant, as the seed parent and *Verbascum phoeniceum* pink, an unpatented plant grown from seed, as the pollen parent. *Verbascum* 'Jackie' is an unpatented plant that originated from a cross between *Verbascum phoeniceum* and *Verbascum dumulosum*.

This new *Verbascum* hybrid is unique in its bright lavender flower color combined with its compact habit and short, multiple flowering stems similar to its parent *Verbascum* 'Jackie'.

This plant is characterized by the following:

1. Large bright lavender flowers.
2. Numerous upright, branching flowering stems.
3. Compact habit.
4. Short flowering stems.
2. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows the whole plant of *Verbascum* 'Lavender Lass' grown in the trial field in bloom in late spring.

DETAILED PLANT DESCRIPTION

The following is a detailed description of the new *Verbascum* selection based on observations of two-year-old specimens grown in the ground in full sun under typical outdoor conditions in the trial fields in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Botanical classification: *Verbascum* hybrid ((*V. phoeniceum*×*dumulosum*)×*V. phoeniceum*).

Variety denomination: 'Lavender Lass'.

Plant:

*Type*.—Herbaceous perennial.
*Form*.—Clumping basal rosette.
*Hardiness*.—U.S.D.A. Hardiness Zones 5–9.
*Size*.—15 to 20 cm tall and 35 cm wide, not including inflorescence.
*Vigor*.—Excellent.
*Roots*.—With one main tap root, and many fibrous lateral branches, White 155A.
*Stem*.—Much congested, 1 cm deep and wide with no space between internodes.

Leaf:

*Type*.—Simple, Evergreen.
*Arrangement*.—Basal.
*Shape*.—Ovate.
*Blade size*.—Grows to 17 cm long and 9.5 cm wide.
*Venation*.—Pinnate.
*Margins*.—Irregularly crenate overall and toothed near base, undulate.
*Apex*.—Acute.
*Base*.—Cuneate.
*Texture*.—Leathery, rugose.
*Surface texture*.—Stellate hairs on both sides.
*Petiole*.—Length — 5.5 cm. Width — Grows to 1 cm. Surface texture — Stellate. Color — Yellow Green 145C.
*Leaf color*.—Abaxial — Deep green. Green 147A with reddish main vein, Greyed Orange 177C. Adaxial — Yellow Green 147C.

Inflorescence:

*Type*.—Panicle.

*Total panicle size.*—30 cm wide and 64 cm high (where flowers are).

*Number of panicles per plant.*—16.

*Cauline leaves.*—5 to 7 in number, 3 to 16.5 cm long and 1.5 to 7.5 cm wide.

*Flower number.*—Count of 380 flowers on one panicle.

*Peduncle.*—Height — 60 to 79 cm. Diameter — 1 cm. near base. Surface texture — Stellate. Color — Yellow Green 146C and D.

*Pedicel.*—Length — 1.3 cm. Surface texture — Glandular hairs. Color — Yellow Green 146A.

*Bloom time.*—May to August in Canby, Oreg.

Flower bud:

*Size.*—1.1 cm. wide and 0.7 cm. deep.

*Description.*—Pentagonal cushion.

*Surface.*—Glandular hairs.

*Color.*—Purple 79C.

Flower:

*Type.*—Perfect, complete, irregular.

*Shape.*—Rotate, irregular, short tubular.

*Size.*—4.5 cm wide and 1 cm deep including stamens.

*Color.*—Purple 78B on both sides.

*Corolla.*—Petal number — 5. Size — 3.5 cm wide and 0.3 cm deep. Surface — Backs with glandular hairs, glabrous inside.

*Calyx.*—Sepal number — 5. Size — 1.1 cm wide and 6 mm deep. Surface texture — Glandular hairs on outside only, glabrous inside. Color — Yellow Green 146A on both sides.

*Stamens.*—Number — 5. Filaments — 8 mm long, Yellow Orange 17B at base and heavily bearded Purple 79B topped with White 155A on upper three stamens. Anthers — Kidney shaped. Greyed Purple 183A and 187A before dehiscence. Pollen — Orange 26A.

*Style.*—1 cm long, Red Purple 71A.

*Stigma.*—Yellow Green 147C.

*Fragrance.*—None.

Fertility: Sterile, no fruit or seed produced.

Disease and pests: *Verbascum* are susceptible to fungal leaf spots and root rots. They need good drainage. Caterpillars may be a problem.

COMPARISONS

This new cultivar is very similar in growth habit and flowering habit to (unpatented). The greatest difference is the flower color. *V.* 'Jackie' is described as having copper colored buds, which open to pale peach colored flowers and lavender stamens. The new cultivar has dark red purple buds that open to bright lavender flowers. *Verbascum* 'Lavender Lass' the same good qualities of numerous flowering stems, short flowering stems, and compact habit of *Verbascum* 'Jackie'.

Compared to *Verbascum* 'Plum Smokey' (U.S. Plant patent application Ser. No. 10/871,831), the new cultivar is taller, and the flowers are a bright lavender rather than a red purple color.

Compared to *Verbascum* 'Sugar Plum' (U.S. Plant patent application Ser. No. 10/871,830), the new cultivar is taller, and the flowers are a bright lavender rather than purple.

I claim:

1. A new and distinct *Verbascum* plant as herein illustrated and described.

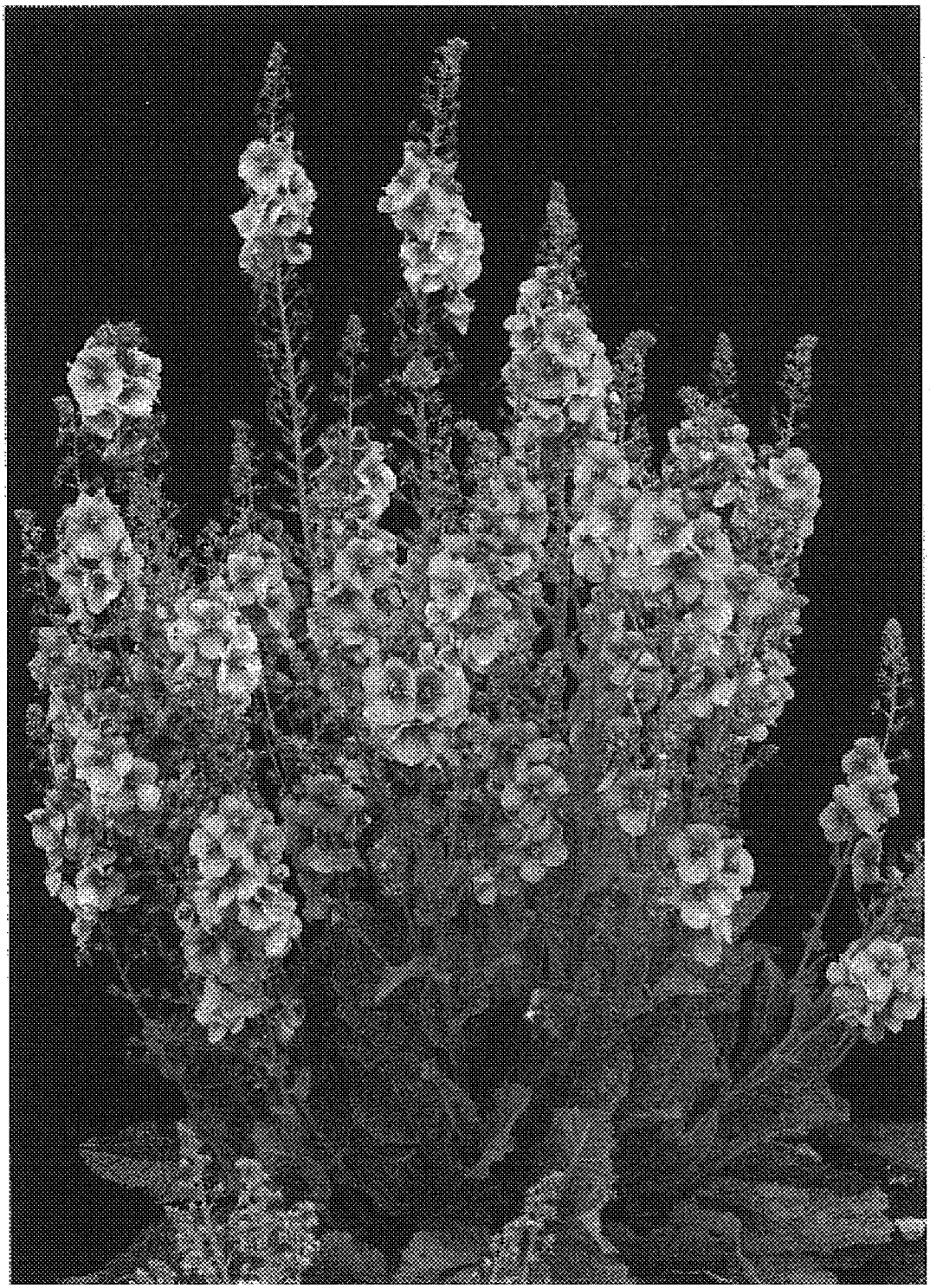

* * * * *